(12) United States Patent
Schöttli

(10) Patent No.: US 6,607,507 B2
(45) Date of Patent: Aug. 19, 2003

(54) SINGLE-USE SYRINGE

(76) Inventor: Theodor Schöttli, Grieshalde 12, CH-8253 Diessenhofen (CH)

( * ) Notice: Subject to any disclaimer, the term of this patent is extended or adjusted under 35 U.S.C. 154(b) by 93 days.

(21) Appl. No.: 09/873,145

(22) Filed: Jun. 2, 2001

(65) Prior Publication Data

US 2001/0041867 A1 Nov. 15, 2001

Related U.S. Application Data

(63) Continuation of application No. PCT/CH99/00576, filed on Dec. 1, 1999.

(30) Foreign Application Priority Data

Jan. 8, 1999 (CH) .............................................. 0030/99
Nov. 5, 1999 (CH) .............................................. 2030/99

(51) Int. Cl.$^7$ .............................................. A61M 5/00
(52) U.S. Cl. ..................... 604/110; 604/111; 604/218; 604/228
(58) Field of Search .................. 604/110, 111, 604/187, 228, 218, 247, 229, 236, 240, 191, 226

(56) References Cited

U.S. PATENT DOCUMENTS

| 4,464,174 | A | * | 8/1984 | Ennis ........................... 604/90 |
| 4,861,335 | A | * | 8/1989 | Reynolds ....................... 604/88 |
| 4,863,427 | A | * | 9/1989 | Cocchi ......................... 604/110 |
| 4,950,240 | A | * | 8/1990 | Greenwood et al. ........ 604/110 |
| 5,000,735 | A | * | 3/1991 | Whelan ....................... 604/110 |
| 5,078,686 | A | * | 1/1992 | Bates ......................... 604/110 |
| 5,163,908 | A |   | 11/1992 | Lambert ...................... 604/110 |
| 5,328,474 | A | * | 7/1994 | Raines ........................ 604/110 |
| 5,921,967 | A | * | 7/1999 | Sadowski et al. ........... 604/218 |
| 6,053,894 | A | * | 4/2000 | Shadd, Jr. ................... 604/191 |
| 6,120,479 | A | * | 9/2000 | Campbell et al. ........... 604/110 |
| 6,302,101 | B1 | * | 10/2001 | Py ........................ 128/200.22 |

FOREIGN PATENT DOCUMENTS

| EP | 0 409 134 A1 | 7/1990 | ............ A61M/5/50 |
| EP | 0 438 453 B1 | 8/1993 | ............ A61M/5/50 |

* cited by examiner

Primary Examiner—Ira S. Lazarus
Assistant Examiner—Tu Cam Nguyen
(74) Attorney, Agent, or Firm—Peter K. Kontler

(57) ABSTRACT

A single-use syringe has a barrel which can constitute a one-piece extrusion, and a shank which is reciprocably guided in the barrel and the distal end of which carries a plunger movable in the barrel toward and away from the needle-carrying front end portion of the barrel. The coupling between the plunger and the shank includes a set of circumferentially spaced-apart breakable spokes which can be of one piece with the distal end of the shank as well as with the plunger. The spokes break not later than when the shank completes a forward stroke during which the plunger expels a flowable substance, such as a medicine, from a chamber located in the barrel between the needle-carrying front end portion and the plunger. The plunger, the spokes and the shank can constitute a one-piece extrusion.

25 Claims, 4 Drawing Sheets

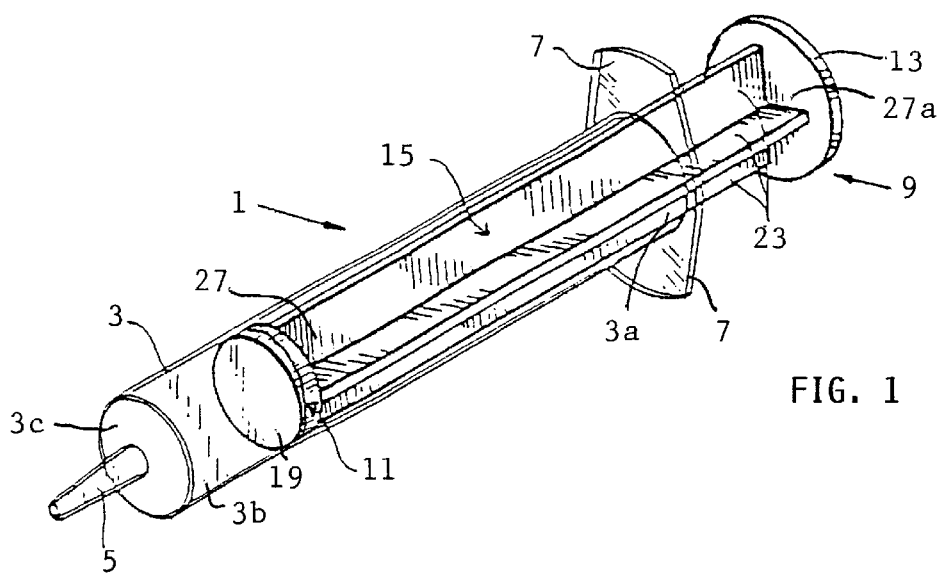
FIG. 1
FIG. 3
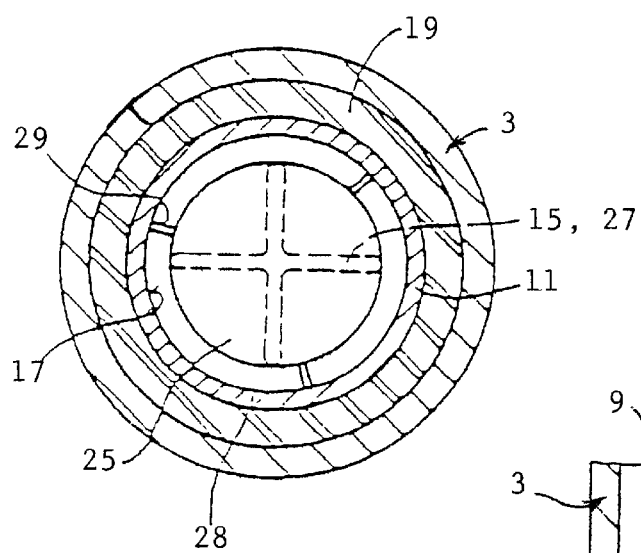
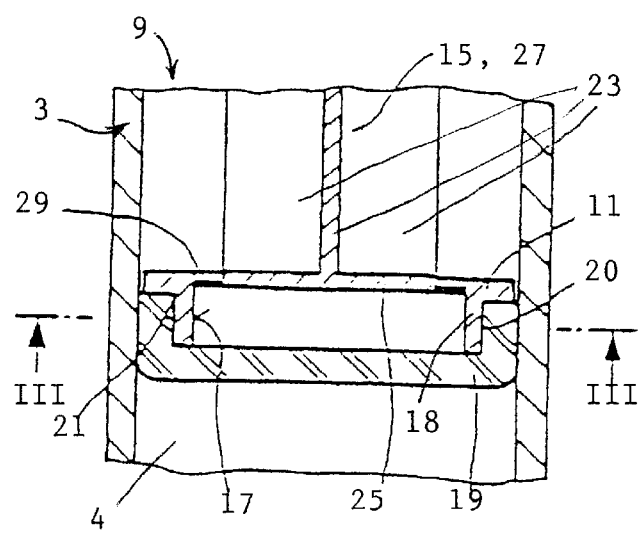
FIG. 2

SINGLE-USE SYRINGE

CROSS-REFERENCE TO RELATED CASES

The present application is a continuation of International Patent Application Serial No. PCT/CH99/00576 filed Dec. 1, 1999. The disclosures of the above-referenced patent applications, as well as that of each US and foreign patent and patent application identified in the specification of the present application, is incorporated herein by reference.

BACKGROUND OF THE INVENTION

The invention relates to improvements in syringes, and more particularly to improvements in so-called single-use or non-reusable syringes.

A single-use syringe is designed in such a way that, once the flowable contents of its cylinder or barrel are evacuated through the needle in response to completion of forward stroke of its piston or plunger, the barrel cannot accept a second supply of flowable material and/or the plunger is incapable of expelling a second quantity of flowable material from the barrel. This is intended to prevent unauthorized persons, especially drug addicts, from reusing the syringe, a practice which is one of the primary reasons for the proliferation of AIDS and many other diseases, especially in countries or towns where the addicts seek to reuse discarded hypodermic syringes for intravenous injection of flowable drugs and/or the addicts share syringes with fellow drug users.

As a rule, a syringe comprises a cylindrical barrel the front end portion of which carries a needle and which confines a reciprocable plunger movable by a piston rod or shank which is accessible at the rear (proximal) end of the barrel. In order to prevent repeated use or uses of such syringes, the plunger is separated from the shank upon completion of its first forward stroke or the plunger cannot be retracted by the shank. In either event, the barrel cannot receive a second supply of a flowable substance. While a physician, a nurse or another trained and authorized person will desist from reusing a syringe, at least without a thorough and reliable sterilization of all parts which come into contact with the substance to be injected and/or with the body of a person who manipulates the syringe or who is to receive an injection, such practice is normally disregarded by many drug addicts so that the prevention of unauthorized use of discarded syringes is a high-priority project for medical and crime combating authorities all over the world.

European patent No. 0 438 453 B1 to Pickhard (published Aug. 18, 1983) discloses a syringe wherein the piston is provided with an axial passage closed by a transverse wall having a weakened portion which is destroyed in response to engagement by a projection provided in the front end portion of the barrel next to the fluid-receiving end of the needle and is intended to destroy the weakened portion while the shank is in the process of carrying out the last stage of its forward stroke. Alternatively, the weakened portion is provided on an insert which is confined in the plunger. Once the weakened portion is destroyed, the internal chamber or space of the barrel in front of the plunger begins to communicate with the atmosphere (by way of one or more radial ports in the plunger and by way of the open rear end of the barrel) so that a next-following retraction of the plunger cannot result in entry of additional flowable material into the barrel in front of the plunger.

It will be seen that the just described patented syringe cannot be reused provided that the first use results in actual destruction of the aforediscussed weakened portion which shares the movements of the plunger. However, a skilled hospital employee or a desperate or poor drug addict can readily acquire the skill which is required to avoid destruction of the weakened portion during the first use as well as during each subsequent use of the syringe. Such unauthorized manipulation is made possible in that a puncturing, a tearing or another mode of destroying the weakened portion necessitates the exertion of a relatively large force so that one seeking to reuse the syringe simply ceases to move the shank forwardly when such person detects or senses the need for the exertion of a greater force in order to continue the forward movement of the shank (i.e., of the plunger). Thus, the patented syringe can be reused as often as desired by the simple expedient of avoiding full depression of the shank and of the plunger toward the needle at the front end of the barrel of such syringe.

U.S. Pat. No. 5,000,735 (granted Mar. 19, 1991 to Whelan) discloses a single-use syringe wherein the plunger is made of rubber and is coupled to an enlarged forward end of the shank by a separately made support ring having breakaway tabs. The tabs are broken off, to thus terminate the motion transmitting connection, during the last stage of forward stroke of the shank relative to the needle-carrying barrel. This ensures that the plunger cannot be retracted away from the needle upon completion of the first and only injection carried out by the patented syringe. A drawback of this proposal is that several constituents of the patented syringe must be made of different materials as well as that the plunger, the shank and the support ring are discrete (separately produced) parts; this contributes to the manufacturing as well as to the assembly cost of such syringes.

U.S. Pat. No. 4,950,240 (granted Aug. 21, 1990 to Greenwood et al.) discloses a single-use hypodermic syringe which constitutes a modification of the syringe disclosed in the aforediscussed US patent to Whelan. The difference is that the shank is initially of one piece with a coupling which secures the plunger to the shank during the initial use of the patented syringe. The coupling is intended to be destroyed during such initial use. This syringe shares the drawbacks of the syringe disclosed in the patent to Whelan. In addition, the assembling of parts into the syringe of Greenwood et al. appears to be rather simple on paper but is quite problematic in actual practice, especially as concerns the ability of the coupling to withstand the stresses during assembly of the syringe, i.e., during the establishment of a breakable connection between the plunger and the shank in such a way that the connection can stand the developing stresses during admission of a flowable medicine or another injectable substance prior to as well as during the first use but to invariably break if one seeks to refill the barrel upon completion of the first use.

U.S. Pat. No. 5,163,908 (granted Nov. 17, 1992 to Lambert) discloses a fail safe composite hypodermic syringe wherein the plunger carries a conical extension bearing a sphere which is initially coupled to pin-shaped segments at the inner side of a hollow shank. Such connection is terminated upon the intended first and only use of the patented syringe. This syringe shares the drawbacks of syringes which are disclosed in the patents to Whelan and Greenwood et al. Moreover, the plunger and the shank of this syringe cannot be made by resorting to simple and inexpensive methods, e.g., to mass production in an injection molding or extruding machine.

Published European patent application Serial No. 0 409 134 A1 of Sempere Escudero (published Jan. 23, 1991) discloses a single-use syringe wherein the plunger is initially coupled to the shank by a breakable annular membrane which is to be destroyed in response to first retraction of the shank, i.e., upon completion of a first injection of flowable material into a living being. To this end, the plunger is captured between a pair of stops which are provided at the inner side of the barrel close to the needle. The drawback of this syringe is the same as that of the syringe disclosed in the aforediscussed European patent No. 0 438 453 B1 to Pickhard, i.e., a skilled nurse or addict can avoid capturing of the plunger between the internal stops of the barrel by the simple expedient of terminating the forward progress of the plunger before the shank reaches its foremost or innermost position.

U.S. Pat. No. 4,863, 427 (granted Sep. 5, 1989 to Cocchi) discloses a single-use syringe wherein a retraction of the plunger subsequent to the first use of the syringe is prevented in that the plunger becomes separated from the reciprocable shank in response to destruction or deactivation of a coupling between such parts, or in response to the establishment of communication between the chamber in front of the plunger and the atmosphere, not later than when the plunger completes its first forward stroke. FIGS. 1 to 3 of this patent show two embodiments of a further modification which appears to be problematic even on paper but appears to be plainly devoid of any utility in actual practice.

OBJECTS OF THE INVENTION

An object of the present invention is to provide a single-use syringe which is more reliable (less likely to be used more than once) than heretofore known single-use syringes.

Another object of the invention is to provide a novel and improved destructible connection or coupling between the piston or plunger and the piston rod or shank of a syringe.

A further object of the instant invention is to provide a single-use syringe which is more reliable and less expensive than heretofore known single-use syringes.

An additional object of the invention is to provide a novel and improved plunger for incorporation into a single-use syringe.

Still another object of the present invention is to provide a novel and improved shank for incorporation into a single-use syringe.

A further object of this invention is to provide a novel and improved method of making a plunger-shank combination for incorporation into a single-use syringe.

Another object of the invention is to provide a single-use syringe wherein a renewed introduction of a flowable substance into the barrel is prevented in a novel, improved and reliable manner.

An additional object of the invention is to provide a single-use syringe which can be employed as a superior substitute for syringes disclosed in the aforediscussed patents and patent applications.

SUMMARY OF THE INVENTION

The invention is embodied in a single-use syringe which comprises an elongated tubular barrel having an open first end portion and a second end portion which is arranged to support a needle (e.g., a needle which is detachable from the barrel), a plunger which is reciprocably received in and defines with the barrel a variable-volume fluid-receiving chamber adjacent the second end portion of the barrel, an elongated shank having a distal end adjacent the plunger and a manually shiftable proximal end at the first end portion of the barrel, and a coupling which connects the plunger with the distal end of the shank. In accordance with a feature of the invention, the coupling includes an array of preferably equidistant circumferentially spaced-apart breakable spokes each of which is or can be of one piece with the plunger as well as with the distal end of the shank.

The arrangement is or can be such that the spokes break in response to movement of the shank toward the second end portion of the barrel to thus cause the plunger to expel fluid from the chamber through the needle at the second end portion of the barrel. Upon breakage of the spokes, the distal end of the shank is movable (a) against the plunger to move the plunger toward the second end portion of the barrel and/or (b) away from the second end portion of the barrel and away from the plunger, i.e., the plunger cannot be used to draw a second supply of flowable material through the needle and into the chamber.

In a presently preferred embodiment of the improved syringe, the plunger is provided with a recess which is arranged to receive the distal end of the shank upon breakage of the spokes in response to further movements of the shank toward the second end portion of the barrel. The recess can constitute a relatively shallow circular blind bore or hole or depression having a diameter greater than that of the distal end of the shank so that such distal end can enter the recess (i.e., the shank can move relative to the plunger in a direction toward the needle) upon breakage of the spokes.

It is within the purview of the invention to provide the plunger with projections, e.g., with at least one for each of the spokes and each integral with the respective spoke at least prior to breakage of of the spokes. The projections are or can be of one piece with the plunger and can extend in the barrel in a direction away from the second end portion of the barrel.

The distribution of the spokes can be such that each spoke extends from the shank at least substantially radially outwardly toward the plunger.

The distal end of the shank can be provided with a disc, and the spokes can extend at least substantially radially of and from the disc toward the plunger.

At least one of the spokes can be provided with surfaces which converge toward each other radially outwardly of the shank and toward the plunger.

The areas of contact of the spokes with the plunger can be smaller than the areas of contact of the spokes with the distal end of the shank.

The spokes can form part of a hollow conical frustum.

In accordance with still another modification, the plunger is spaced apart from the distal end of the shank and the spokes are elongated and extend longitudinally or substantially longitudinally of the shank between the distal end of the shank and the plunger.

The aforementioned recess of the plunger can be bounded by a conical surface which is connected with the spokes at least until the spokes are caused to break.

In accordance with an additional modification, the plunger includes a first portion which is connected with the distal end of the shank by the aforementioned spokes, and a second portion which at least partially surrounds the first portion at sealingly engages the barrel. The second portion of the plunger can resemble or constitute a cup having a cylindrical sidewall which surrounds the first portion.

The internal surface of the barrel can be configurated in such a way that it includes a first portion offering a relatively low first resistance to movements of the plunger toward and away from the second end portion of the barrel, and at least one second portion which offers a greater second resistance to such movements of the plunger. The at least one second portion of the internal surface can be provided on an annular internal constriction of the barrel; such internal constriction fully or at least partially surrounds the shank. For example, the constriction can include a circumferentially complete collar extending radially inwardly from the first portion of the internal surface.

The barrel can be provided with a cylindrical internal surface along which the plunger is slidable toward and away from the second end portion of the barrel. Such internal surface can include an at least substantially frustoconical portion which is adjacent to and tapers toward the second end portion of the barrel and serves to offer a progressively increasing resistance to movement of the plunger toward the second end portion of the barrel.

The barrel can constitute a one-piece extrusion. Analogously, the shank, the spokes and at least a portion of the plunger can also constitute a one-piece extrusion.

Furthermore, at least a portion of the plunger can consist of a resilient material and at least a portion of the shank can have a substantially or exactly cruciform cross-sectional outline.

The syringe can be provided with means (e.g., a disc) for preventing tilting of the plunger in the barrel, especially upon breakage of one or more spokes.

The novel features which are considered as characteristic of the invention are set forth in particular in the appended claims. The improved syringe itself, however, both as to its construction and the modes of making, assembling and utilizing the same, together with numerous additional important and advantageous features and attributes thereof, will be best understood upon perusal of the following detailed description of certain presently preferred specific embodiments with reference to the accompanying drawings.

BRIEF DESCRIPTION OF THE DRAWINGS

FIG. 1 is a perspective view of a single-use syringe which embodies one form of the present invention, the plunger and the shank being shown in intermediate positions which they can assume during the first and only possible injection of a flowable substance into the body of a human or animal being;

FIG. 2 is an enlarged fragmentary axial sectional view of the plunger and of adjacent portions of the shank and barrel of the syringe shown in FIG. 1;

FIG. 3 is a transverse sectional view as seen in the direction of arrows from the line III—III shown in FIG. 2;

DESCRIPTION OF PREFERRED EMBODIMENTS

Figure 4:
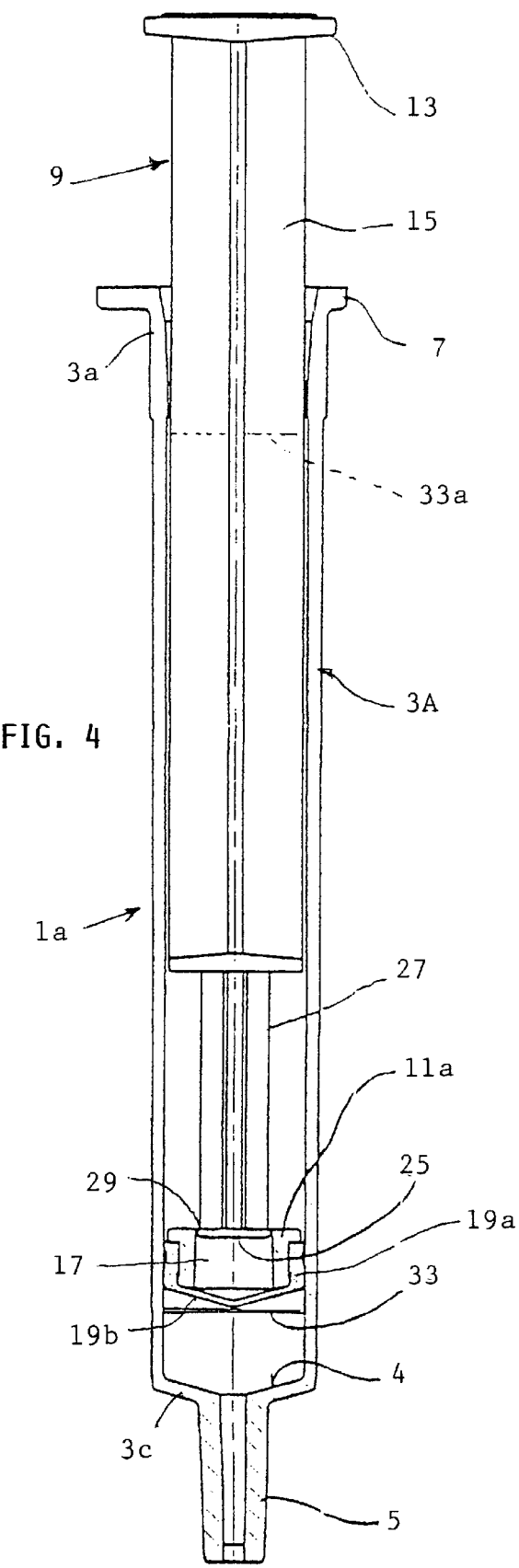
FIG. 4 is a larger-scale elevational view of a second syringe having a modified plunger, with the barrel shown in an axial sectional view and with the plunger and shank shown in axial positions similar to or identical with those of the corresponding parts shown in FIG. 1.

FIG. 1 shows a single-use syringe 1 which comprises an elongated tubular (preferably cylindrical) barrel 3 having an open first or rear end portion 3a provided with two finger grips 7, and a second or front end portion 3b provided with a forwardly extending coaxial conical connecting member 5 for a needle (not shown). A conical connecting member constitutes but one form of the means for securing the needle to the barrel 3; reference may be had, for example, to the aforediscussed U.S. Pat. No. 5,163,908 to Lambert which discloses a threaded connection between a needle guard and a needle base.

The barrel 3 receives an elongated piston rod or shank 9 (hereinafter called shank for short) having a distal end 27 which is confined in the barrel and carries a piston or plunger 11 (hereinafter called plunger), and a proximal end 27a which is shown as being of one piece with a thumb rest 13. FIG. 1 shows the shank 9 in a partly depressed position in which the plunger 11 is spaced apart from the two end portions 3a, 3b of the barrel 3. The means for coupling the plunger 11 to the distal end 27 of the shank 9 is constructed and is assembled with the parts 9, 11 in accordance with a first embodiment of the present invention and is shown in detail in FIGS. 2 and 3.

The major part 15 of the illustrated shank 9 has a cruciform cross-sectional outline. In accordance with a feature of the invention, the barrel 3 of the syringe 1 is of one piece and is preferably a mass-produced plastic part turned out by an injection molding machine. The shank 9, the plunger 11 and the coupling between the parts 9, 11 together constitute a second one-piece part which is or which can be turned out in an injection molding or an analogous mass-producing machine. The barrel 3 is or can be made of a transparent or translucent material.

As can be seen in FIG. 2, that side of the plunger 11 which faces toward the proximal end 27a of the shank 9 is provided with a coaxial cylindrical recess 17 surrounded by a cylindrical collar 18 having a cylindrical external surface 20 which is a press fit in a complementary cylindrical internal surface of a cupped sealing element 19 having a relatively short cylindrical wall surrounding the major portion of the collar 18. The sealing element 19 has a cylindrical external surface which slidably but sealingly engages the internal surface of the barrel 3. The exposed front end face of the sealing element 19 and that portion of the internal surface of the barrel 3 which is disposed between the plunger 11 and the end wall 3c at the front end portion 3b surround a chamber 4 which confines a supply of a flowable material (such as a liquid medicine) which is injected into a vein or into another part of a human or animal body during the first and only use of the syringe 1.

The rear end of the recess 17 is sealed by a disc-shaped portion 25 (hereinafter called disc) of the shank 9; this disc has a diameter (see FIG. 3) which is smaller than the inner diameter of the collar 18. The peripheral portion of the disc 25 is connected with the collar 18 by an annular array of radially extending weakened portions 29 (hereinafter called spokes for short) which constitute the aforementioned coupling between the shank 9 (and more specifically the disc 25 of the shank) and the plunger 11. The spokes 29 extend radially of the disc 25 and are caused to break when the shank 9 encounters a predetermined minimum resistance to further forward movement toward the front end portion 3b of the barrel 3.

The characteristics of the spokes 29 can be readily selected in such a way that they invariably break when the sealing element 19 abuts the front end wall 3c of the barrel 3 but the user of the syringe 1 continues to push the thumb rest 13 forwardly toward the front end portion 3b of the barrel. Breakage of the spokes 29 enables the distal end 27 (including the disc 25) of the major portion 15 of the shank 9 to penetrate into the recess 17 and to advance into abutment with the inner side of the disc-shaped major portion of the cupped sealing element 19. The latter preferably consists of rubber or a suitable elastomeric plastic material.

If an authorized or unauthorized user of the syringe 1 retracts the shank 9 to or beyond the intermediate position shown in FIG. 1 or 2 subsequent to breakage of the spokes 29, such movement of the shank is shared by the disc 25 but not by the plunger 11 and its sealing element 19, i.e., the chamber 4 cannot be refilled with an injectable fluid. Otherwise stated, once the spokes 29 are destroyed (this takes place during the last stage of forward movement of the shank 9 or upon completion of forward movement of the sealing element 19), the syringe 1 must be discarded because it cannot be refilled with a flowable substance so that it is useless to an unskilled or careless nurse or a physician as well as to an unauthorized person (such as a drug addict who cannot or does not desire or afford to use a fresh syringe).

FIG. 3 shows that the intact spokes 29 are relatively narrow webs which are separated from each other by arcuate clearances 28 extending between the plunger 11 and the periphery of the disc 25.

Referring again to FIG. 2, it will be seen that the cylindrical rear portion of the sealing element 19 abuts the annular surface 21 at the front side of the plunger 11, preferably with a force which is required to ensure that the disc 25 and the piston 11 cannot move axially relative to each other except upon destruction of the spokes 29. Therefore, the sealing element 19 of FIGS. 2 and 3 can be said to form part of the plunger 11.

As can be seen in FIG. 2, the four elongated walls 23 of the portion 15 of the shank 9 do not extend radially beyond the periphery of the disc 25 so that the front ends of the walls 23 can enter the recess 17 with the disc 25 when the spokes 29 are destroyed and the shank 9 continues to move toward the end wall 3c of the barrel 3. However, it is equally within the purview of the invention to employ a shank wherein the front ends of the walls do not extend radially all the way to the periphery of the disc 25, as long as the diameter of the surface surrounding the recess 17 exceeds that of the disc.

The illustrated spokes 29 are narrow and thin radially extending strips or bars or plates or films which, in the embodiment of FIGS. 1 to 3, extend from the periphery of the disc 25 to the plunger 11. It is equally possible to provide such spokes between the front end portions (at 27) of the walls 23 and the plunger 11. It is also possible to employ spokes which have oval, round or other suitable cross-sectional outlines, i.e., other than rectangular outlines similar to those of the illustrated spokes 29. Still further, the radially outer ends of the spokes 29 (or of their equivalents) can be confined in the recess 17 rather than being disposed at the rear end of such recess as shown in FIG. 2.

The stability of the spokes 29 (or of their equivalents) is selected in such a way that they break when the force with which the shank 9 is moved forwardly (i.e., toward the end wall 3c of the barrel 3) exceeds a predetermined value, e.g., 10 N. The breaks can take place at the radially inner and/or at the radially outer ends of the spokes or across intermediate portions of the spokes.

Figure 5:
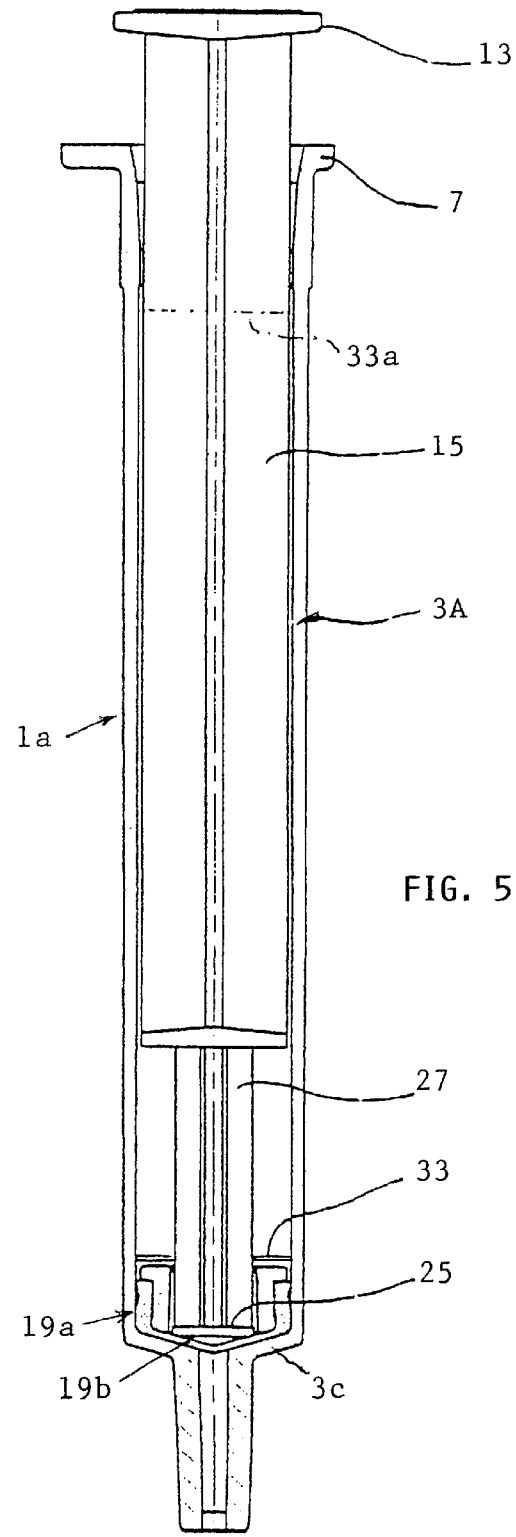
FIG. 5 is a view corresponding to that of FIG. 4 but with the plunger and shank shown in their fully extended positions in which the coupling between the plunger and the shank is destroyed.

The syringe 1a of FIGS. 4 and 5 differs from the syringe 1 of FIGS. 1 to 3 in that the internal surface of the barrel 3A is provided with at least one internal constriction 33 serving to increase the magnitude of the force which is required to move the plunger 11a and its modified cupped resilient sealing element 19a toward the front end wall 3c of the barrel. The provision of such constriction (which can but need not be a circumferentially complete annular constriction) even more reliably ensures that the spokes 29 break before the volume of the chamber 4 is reduced to a minimum value.

In addition, the constriction 33 is provided at an axial distance from the end wall 3c which exceeds the axial dimen of the plunger 11a inclusive of its sealing element 19a. Thus, once the shank 9 moves to the axial position of FIG. 5 (in which the conical front end wall 19b of the sealing element 19a abuts the end wall 3c), the constriction 33 acts as a barrier against retraction of the plunger 11a to and beyond the axial position of FIG. 4. The radial width of the constriction 33 can be small or very small and normally depends upon the inner diameter of the barrel 3A.

FIGS. 4 and 5 further shown a second internal constriction 33a which is close to the open rear end portion 3a of the barrel 3A. The constriction 33a can serve as a means for limiting, or indicating the reaching of the end of, the required or desired or acceptable rearward stroke of the shank 9. Such end of rearward stroke of the shank 9 is reached when the sealing element 19a abuts the constriction 33a.

Figure 6:
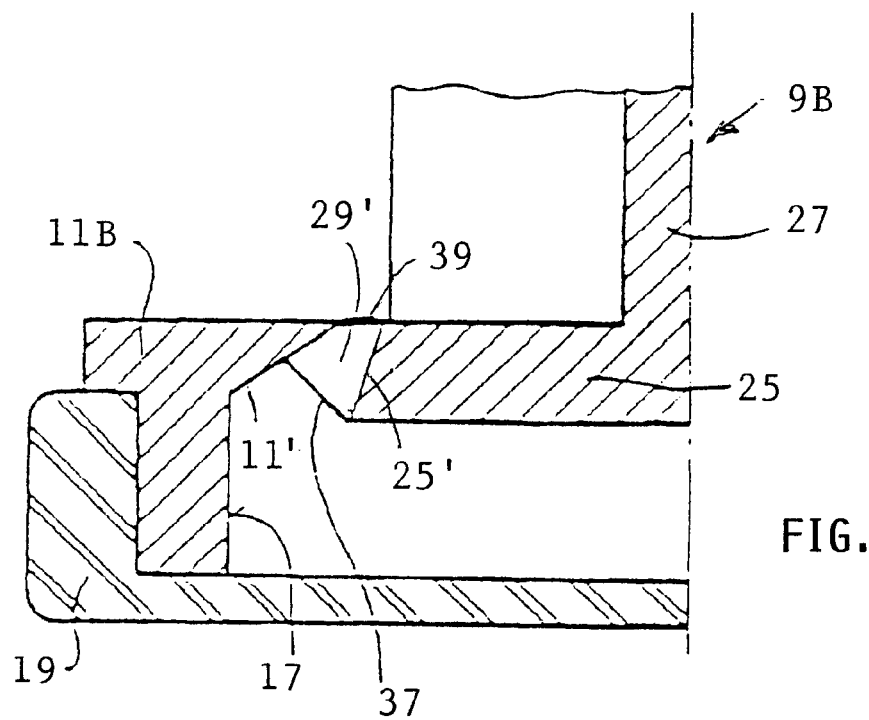
FIG. 6 is a fragmentary axial sectional view of a plunger, of a shank and of a modified coupling between such parts, the coupling being shown in a condition it assumes prior to completion of forward stroke of the shank.

FIG. 6 illustrates a portion of a modified syringe wherein the spokes 29' which connect the disc 25 of the distal end 27 of the shank 9B with a plunger 11B have rearwardly sloping front edge faces 37 located in the recess 17 of the plunger. The spokes 29' have polygonal (such as rectangular or square) cross-sectional outlines. The rear surface 39 of the spoke 29' shown in FIG. 6 is parallel to the rear side of the plunger 11B, i.e., it extends exactly radially of the axis of the shank 9B. The disc 25 has a frustoconical peripheral or external surface 25' from which the illustrated spoke 29' extends toward the conical internal surface 11' of the plunger 11B.

Figure 7:
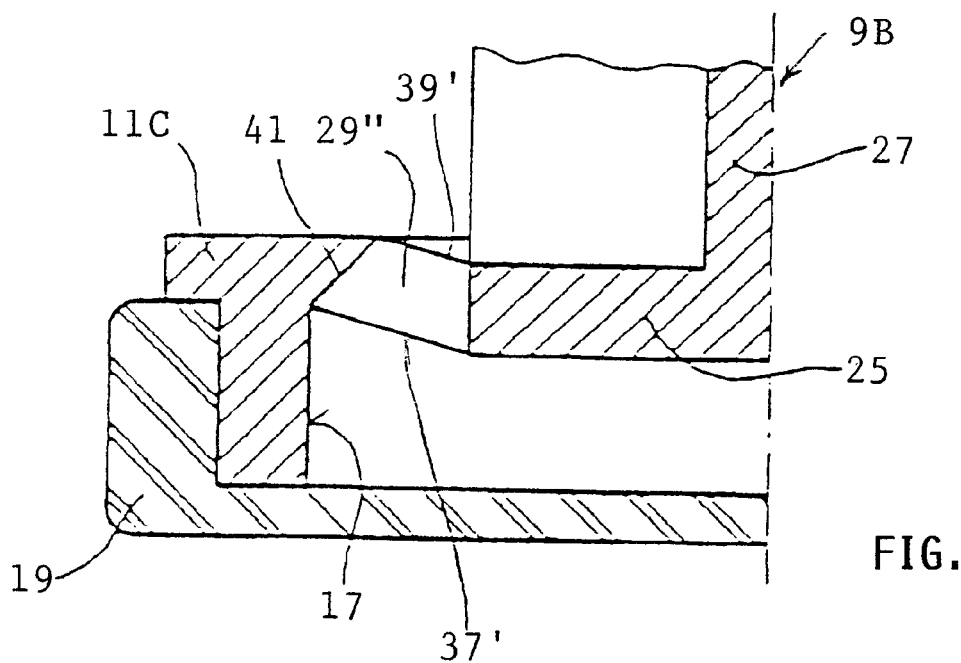
FIG. 7 is a similar view of a structure constituting a modification of that shown in FIG. 6.

In FIG. 7, the front edge face or surface 37' of the illustrated spoke 29" is at least substantially parallel to the rear edge face 39'. The plunger 11C has a frustoconical internal surface 41 from which the spokes 29" extend radially inwardly toward the disc 25. The structure which is shown in FIG. 7 can employ three equidistant at least substantially radially extending spokes 29".

Figure 8:
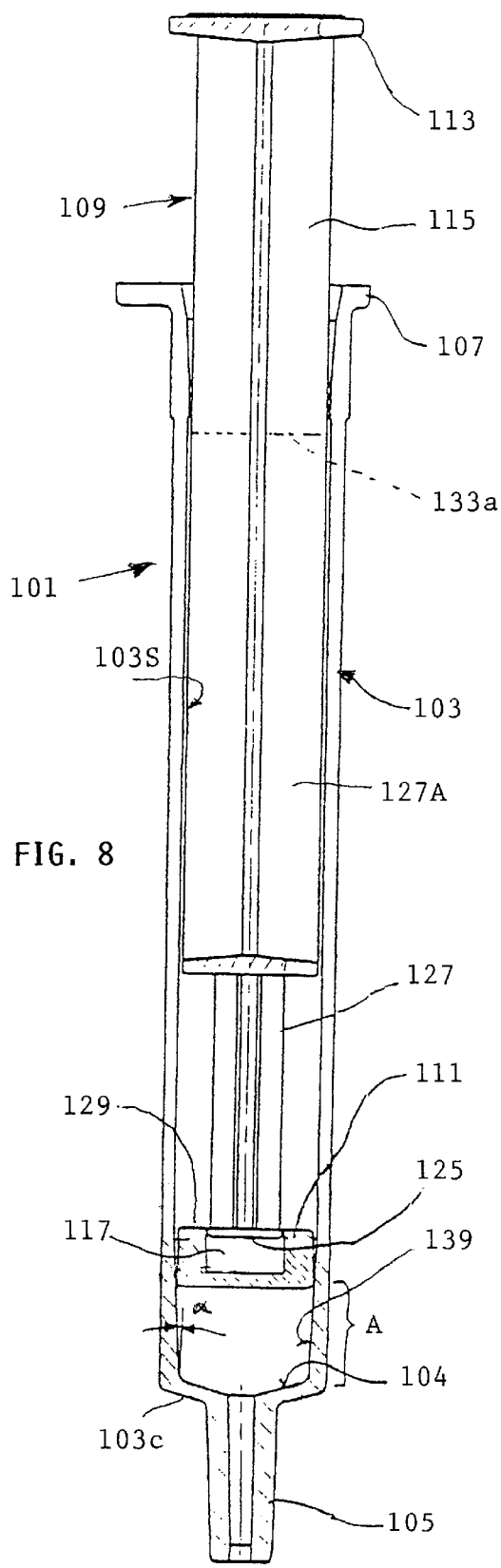
FIG. 8 is a view similar to that of FIG. 4 but showing a different coupling between the shank and the plunger.

Those parts of the syringe 101 shown in FIG. 8 which are identical with or plainly analogous to the corresponding parts of the syringe 1 of FIGS. 1 to 3 are denoted by similar reference characters plus 100. A difference between the shanks 9 and 109 of the syringes 1 and 101 is that the radial extension of the front end portion or distal portion 127 of the shank 109 is less than the radial extension of the rear or proximal portion 127A, i.e., only the portion 127A is slidably guided in the barrel 103.

The preferably elastic plunger 111 at the distal end or portion 127 of the shank 109 is a one-piece body which is separably secured to the shank 109 by an array of radially extending (preferably but not necessarily equidistant) spokes 129. The peripheral surface of the one-piece plunger 111 is in direct sliding but sealing engagement with the internal surface 103S of the barrel 103. The blind bore or hole or recess 117 of the plunger 111 receives the disc 125 of the shank 109 when the spokes 129 break and the shank continues to move forwardly toward the front end wall 103c of the barrel 103.

That end portion A of the cylindrical part of the barrel 103 which is adjacent the front end wall 103c has a frustoconical internal surface 139 which constitutes the foremost portion of the internal surface 103S and tapers toward the end wall 103c. The rather minor inclination of the frustoconical internal surface 139 with respect to the cylindrical internal surface 103S of the barrel 103 is indicated by the small acute angle α. When the plunger 111 reaches the conical internal surface 139 and continues to move forwardly toward the end wall 103c, it encounters a progressively and preferably gradually increasing resistance to forward movement, and the spokes 129 ultimately break to thus separate the plunger 111 from the shank 109. Thus, the frustoconical surface 139 constitutes another embodiment of a constriction which induces the spokes 129 to break before the shank 109 reaches its fully extended front end position.

Figure 9:
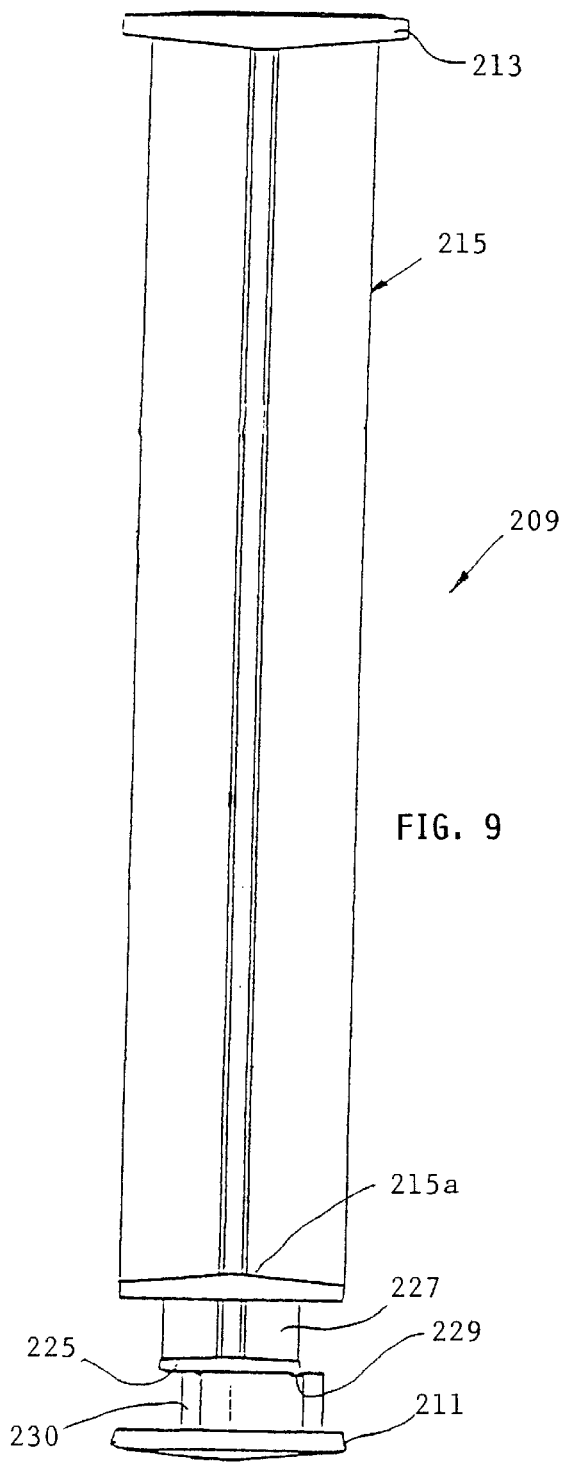
FIG. 9 is an elevational view of a shank, of a plunger and of a modified coupling between such parts.

FIG. 9 shows a shank 209 which has a set of walls 215 and a thumb rest 213. The front or distal end 227 of the shank 209 carries a disc 225 which is connected with rearwardly extending axially parallel projections or lets 230 of the plunger 211 by breakable spokes 229. The plunger 211 is a simple flat disc having a peripheral surface in sliding but sealing engagement with the internal surface of the barrel (not shown) partially confining the shank 209 of FIG. 9. The plunger 211 is provided with three preferably equidistant at least substantially axially parallel rearwardly extending projections or legs 230 each of which is of one piece with the respective spoke 229 until and unless the spoke is destroyed in response to the application to the thumb rest 213 of a predetermined force while the shank 209 encounters a predetermined resistance against further forward movement toward the needle on the front end wall of the respective barrel. The axial distance of the disc-shaped plunger 211 from the disc 225 preferably matches or approximates the axial distance between the disc 225 and the transverse wall member 215a at the front ends of the walls 215 forming part of the plunger 209.

Certain presently preferred modes of making, assembling and utilizing the syringe 1 of FIGS. 1 to 3 are as follows:

The two discrete parts 3 and 9 of the syringe 1 are preferably made in an injection molding or equivalent machine. The barrel 3 is of one piece with the thumb rest 13 and with the end wall 3c, and the shank 9 is of one piece with the plunger 11 which latter carries the sealing element 19. The spokes 29 are assumed to be intact, i.e., the disc 25 of the shank 9 is still of one piece with the plunger 11. Thus, the syringe 1 need not comprise more than three discrete parts, namely the barrel 3, the combination of the shank 9, plunger 11 and the coupling including the spokes 29, and the sealing element 19.

The shank 9 is inserted into the barrel 3 and is pushed forwardly to a predetermined position (or to one of a preselected range of predetermined positions) short of the front end wall 3c of the barrel 3, i.e., to an axial position in which the spokes 29 are still intact. For example, and if the barrel 3 of the syringe 1 shown in FIGS. 1 to 3 employs a front or distal constriction 33 of the type shown in FIGS. 4 and 5, the shank 9 is brought to a halt when the sealing element 19 of the piston 11 is close to but out of contact with the constriction 33. Introduction of the shank 9 into the barrel 3 is normally effected by resorting to a suitable assembling or handling unit, not shown; such apparatus renders it possible to select the foremost position of the shank 9 with a high or very high degree of accuracy and reproducibility.

If the syringe 1 employs a plunger 109 of the type shown in FIG. 8 or a plunger 209 of the type shown in FIG. 9, i.e., if the piston (111 or 211) does not include a separately produced sealing element 19 or 19a, the shank 109 or 209 is immediately ready to enter the barrel 3 as soon as it is withdrawn or ejected from the making (such as injection molding) machine, i.e., the step of making the sealing element 19 or 19a and the step of mounting such sealing element on the plunger 11 can be dispensed with.

The plunger 11 of FIGS. 1 to 3 can move forwardly until its sealing element 19 comes in contact with the inner side of the end wall 3c. The next step involves retraction of the shank 3 so that the plunger 11 can draw a supply of a selected fluid medium either through the needle (not shown) or directly through the needle connector 5 if the needle is not yet affixed to such connector. The just described chamber filling step can be followed by the step of expelling air (if any) from the chamber 4 prior to introduction of the needle into a selected portion (e.g., into a vein) of a human or animal body and the next-following injection of the flowable substance (such as a medication) into the selected portion of the body. The injecting step is or can be completed when the sealing element 19 of the plunger 11 comes into abutment with the front end wall 3c of the barrel 3. If the barrel 3 is provided with an internal constriction 33 of the type shown in FIGS. 4 and 5, the plunger 11 begins to encounter an increased opposition to further forward movement at a time when its sealing portion 19 is still remote from the front end wall 3c. The axial position of the constriction 33 can be selected in such a way that the plunger 11 encounters a greater resistance to further forward movement in the barrel 3 when the sealing element 19 is located at a distance of one or more millimeters from the front end wall 3c.

Any further forward movement or attempt at a further forward movement results in a breakage of the spokes 29 and in desired separation of the plunger from the distal end 27 of the shank 9.

An important advantage of the illustrated design of the improved syringe is that the plunger can continue to expel a predetermined quantity of fluid medium from the chamber 4 in spite of (i.e., subsequent to) the breakage of the spokes 29. This is due to the fact that the distal end 27 of the shank 9 is then free to push the disc 25 into the recess 17 and to continue the advan-cement of the freshly separated plunger 11 (and more specifically of the sealing element 19) toward and into actual contact with the front end wall 3c.

A subsequent retraction of the shank 9 cannot result in introduction (by suction) of fresh flowable material into the chamber 4 because the rearwardly advancing shank is fully separated from the plunger and its sealing element.

To summarize, the improved syringe exhibits at least some of the following important advantages:

The cost of making syringe is a fraction of the cost of making many presently known single-use syringes. Thus, if the improved syringe employs a one-piece plunger (see the plunger 111 of FIG. 8 or the plunger 211 of FIG. 9), the entire syringe consists of only two parts, namely the barrel (such as 103) and the combined plunger (111) and shank (109). The cost is increased only negligibly if the sealing element (such as 19 shown in FIGS. 1 to 3) is a separately (mass-) produced part made of rubber or another suitable elastomeric material. The assembly of a bipartite or tripartite syringe is a simple and hence inexpensive procedure.

The improved syringe is highly reliable in each and every important respect. Thus, and referring again to FIG. 4, the introduction of a requisite amount of flowable material into the chamber 4 (by way of the hollow connector 5) merely involves a retraction of the plunger 11a from the axial position actually shown in FIG. 4 (i.e., rearwardly of the constriction 33) to a position forwardly of and normally close to the constriction 33a. Expulsion of the flowable substance from the chamber 4 takes place while the shank 9 of FIG. 4 is caused to move forwardly from the constriction 33a toward the constriction 33 as well as thereafter, i.e., subsequent to breakage of the spokes 29 while the disc 25 moves into the recess 17 toward and thereupon with the conical bottom end wall 19b of the sealing element 19a (see FIG. 5). Return movement of the plunger 11a and of the sealing element 19a from the positions shown in FIG. 5 is prevented on two grounds, namely (a) because the spokes 29 are destroyed so that the shank 9 is free to move rearwardly relative to the plunger 11a, and (b) because the plunger 11a is intercepted by the constriction 33.

The constrictions 33, 33a constitute an optional but highly desirable advantageous feature of the improved syringe. This holds especially true for the constriction 33 at the front end portion of the barrel; such constriction performs the important functions of reliably ensuring breakage of the spokes (such as the spokes 29 shown in FIG. 4) during expulsion of the contents of the chamber 4 into the body of a patient, and of reliably preventing retraction of the plunger 11a from the position shown in FIG. 5. As a rule, a physician or a nurse will be expected or will desire to expel the entire fluid contents of the chamber 4 into a patient; such person in charge will readily recall that, if the syringe is of the type shown in FIGS. 4 and 5, a rise in resistance of the shank 9 to further advancement into the barrel 3A must be overcome if the entire contents of the chamber are to be expelled from the barrel, i.e., that the injection of the flowable substance is terminated when the shank 9 has reached the end of its forward stroke. For example, the constriction 33 can be provided at a distance of 4–5 mm from the front end wall 3c of the barrel 3A shown in FIGS. 4 and 5.

Attempts to permit or facilitate or effect the aspiration of a second quantity of a flowable substance into the chamber 4 of the barrel 3A (e.g., by a drug addict who has gained access to a spent syringe 1a of the type shown in FIGS. 4 and 5) are to no avail. For example, if an unauthorized person attempts to push the sealing element 19a away from the front end wall 3c by resorting to a nail or a piece of wire, such undertaking cannot result in the flow of a fluid up the connector 5 while the connector is being used to guide the wire or nail in a direction to push the sealing element 19a and the other part or parts of the plunger 11a rearwardly.

In order to avoid a tilting of the plunger (such as the plunger 11a shown in FIGS. 4 and 5) in the barrel 3A, e.g., upon breakage of fewer than all of the spokes 29 (such as upon breakage of one or two out of a total of three spokes) when the plunger is being acted upon by asymmetrically distributed forces, the plunger can be provided with a disc-shaped guide (not specifically shown) which is dimensioned to permit a movement of the plunger in an orientation as shown in FIGS. 4 and 5 but to prevent any movements of the plunger in other orientation(s) relative to the barrel 3A and shank 9.

The rear constriction 33a in the barrel 3A of FIGS. 4 and 5 serves primarily as an indicator that the chamber 4 of the barrel contains a desired (i.e., a prescribed or an optimum) quantity of flowable material which is to be injected into a human or animal body.

The following undertaking can constitute an additional step which even more reliably ensures adequate filling of the barrel with a flowable substance as well as a reliable breakage (destruction) of the spokes when the injection of the flowable material into a human or animal body is completed: The configuration and/or orientation and/or distribution and/or the number of spokes can be readily selected in such a way that the spokes offer a greater resistance to breakage during a first retraction of the shank for the purpose of drawing a metered quantity of flowable material into the chamber of the barrel, and that the spokes offer a lesser resistance to breakage during subsequent (first) forward stroke of the shank. For example, this can be readily accomplished with spokes (29', 29") of the type shown in FIGS. 6 and 7. To this end, the characteristics of the spokes 29' and/or 29" can be selected with a view to ensure that such spokes break in response to the application (to the shank 9B) of a forwardly oriented axial force within the range of between about 7 and 10 N. The force which must be applied to move the (still intact) shank 9B rearwardly (in order to draw fluid into the chamber of the barrel) can be well above the aforementioned range in order to ensure that the shank 9B will invariably draw a requisite quantity of fluid (e.g., a medication) into the chamber of the barrel for the shank 9B of FIG. 6 or 7.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art of single-use syringes and, therefore, such adaptations should and are intended to be comprehended within the meaning and range of equivalence of the appended claims.

What is claimed is:

1. A single-use syringe, comprising:
   an elongated tubular barrel having an open first end portion and a second end portion arranged to support a needle;
   a plunger reciprocably received in and defining with said barrel a variable-volume fluid-receiving chamber adjacent said second end portion of the barrel;
   an elongated shank having a distal end adjacent said plunger and a manually shiftable proximal end at the first end portion of said barrel; and
   a coupling connecting said plunger with said distal end of said shank, said coupling including an array of circumferentially spaced-apart breakable spokes each of which is of one piece with said plunger and with said distal end of said shank.

2. The syringe of claim 1, wherein said spokes are arranged to break in response to movement of said shank toward said second end portion of said barrel to thus cause said plunger to expel fluid from said chamber through the needle at said second end portion of the barrel.

3. The syringe of claim 2 wherein, upon breakage of said spokes, said distal end of said shank is movable (a) against said plunger to move the plunger toward the second end portion of said barrel, and (b) away from said second end portion of said barrel and away from said plunger.

4. The syringe of claim 3, wherein said plunger has a recess which is arranged to receive said distal end of said shank upon breakage of said spokes in response to further movement of said shank toward said second end portion of said barrel.

5. The syringe of claim 4, wherein said recess is a circular recess having a first diameter and said distal end of said shank has a second diameter less than said first diameter so that said distal end can enter said recess upon breakage of said spokes.

6. The syringe of claim 3, wherein said plunger has projections, at least one for each of said spokes and each integral with the respective spokes at least prior to breakage of said spokes.

7. The syringe of claim 6, wherein said projections are of one piece with said plunger and extend in said barrel in a direction away from said second end portion of said barrel.

8. The syringe of claim 1, wherein said spokes extend from said shank at least substantially radially outwardly toward said plunger.

9. The syringe of claim 1, wherein said distal end of said shank includes a disc and said spokes extend at least substantially radially outwardly of and from said disc toward said plunger.

10. The syringe of claim 1, wherein at least one of said spokes has surfaces which converge toward each other radially outwardly of said shank and toward said plunger.

11. The syringe of claim 1, wherein the areas of contact of said spokes with said plunger are smaller than the areas of contact of said spokes with said distal end of said shank.

12. The syringe of claim 1, wherein said spokes form part of a hollow conical frustum.

13. The syringe of claim 1, wherein said plunger has a recess and said spokes are disposed in said recess not later than upon breakage of said spokes in response to further movement of said shank toward said second end portion of said barrel.

14. The syringe of claim 1, wherein said plunger is spaced apart from said distal end of said shank and said spokes are elongated and extend longitudinally of the shank between said distal end and said plunger.

15. The syringe of claim 1, wherein said plunger has a recess and a conical surface bounding said recess, said conical surface being connected with said spokes at least prior to breakage of the spokes.

16. The syringe of claim 1, wherein said plunger includes a first portion connected with the distal end of said shank by said spokes, and a second portion at least partially surrounding said first portion and sealingly engaging said barrel.

17. The syringe of claim 16, wherein said second portion of said plunger is cup-shaped.

18. The syringe of claim 1, wherein said barrel has an internal surface including a first portion offering a first resistance to movements of said plunger toward and away from said second end portion of said barrel, and at least one second portion offering a greater second resistance to said movements of said plunger.

19. The syringe of claim 18, wherein said at least one second portion of said internal surface is provided on an annular internal constriction of said barrel, said at least one constriction at least partially surrounding said shank.

20. The syringe of claim 1, wherein said barrel has an internal surface along which said plunger is slidable toward and away from said second end portion of the barrel, said internal surface having an at least substantially frustoconical portion adjacent to and tapering toward said second end portion of said barrel to offer a progressively increasing resistance to movement of said pluger toward said second end portion of said barrel.

21. The syringe of claim 1, wherein said barrel is a one-piece extrusion.

22. The syringe of claim 1, wherein said shank, said spokes and at least a portion of said plunger constitute a one-piece extrusion.

23. The syringe of claim 1, wherein at least a portion of said plunger consists of a resilient material.

24. The syringe of claim 1, wherein at least a portion of said shank has an at least substantially cruciform cross-sectional outline.

25. The syringe of claim 1, further comprising means for preventing tilting of said plunger in said barrel.

* * * * *